US008609905B2

(12) United States Patent
Ohnishi et al.

(10) Patent No.: US 8,609,905 B2
(45) Date of Patent: Dec. 17, 2013

(54) METHOD FOR PRODUCING GLYCEROL

(75) Inventors: Hiroshi Ohnishi, Wakayama (JP);
Hiroshi Danjo, Wakayama (JP)

(73) Assignee: Kao Corporation, Tokyo (JP)

( * ) Notice: Subject to any disclaimer, the term of this patent is extended or adjusted under 35 U.S.C. 154(b) by 251 days.

(21) Appl. No.: 13/142,082

(22) PCT Filed: Dec. 21, 2009

(86) PCT No.: PCT/JP2009/071825
§ 371 (c)(1),
(2), (4) Date: Jun. 24, 2011

(87) PCT Pub. No.: WO2010/074291
PCT Pub. Date: Jul. 1, 2010

(65) Prior Publication Data
US 2011/0263908 A1 Oct. 27, 2011

(30) Foreign Application Priority Data

Dec. 25, 2008 (JP) .................................. 2008-329394
Dec. 1, 2009 (JP) .................................. 2009-273355

(51) Int. Cl.
*C07C 27/00* (2006.01)

(52) U.S. Cl.
USPC ...................................................... 568/858

(58) Field of Classification Search
None
See application file for complete search history.

(56) References Cited

U.S. PATENT DOCUMENTS

| 6,407,269 | B2 * | 6/2002 | Kaita et al. ................ 554/167 |
| 2001/0042340 | A1 | 11/2001 | Tateno et al. | |
| 2002/0010359 | A1 | 1/2002 | Kaita et al. | |
| 2007/0158270 | A1 | 7/2007 | Geier et al. | |
| 2009/0030243 | A1 | 1/2009 | Soest et al. | |
| 2009/0105492 | A1 | 4/2009 | Nomura et al. | |

FOREIGN PATENT DOCUMENTS

| CN | 101331217 A | 12/2008 |
| EP | 1 978 009 A1 | 10/2008 |
| FR | 2698101 A1 | 5/1994 |
| JP | 30-5618 B | 8/1955 |
| JP | 6-184024 A | 7/1994 |
| JP | 6-313188 A | 11/1994 |
| JP | 10-218810 A | 8/1998 |
| JP | 2001-17862 A | 1/2001 |
| JP | 2001-302584 A | 10/2001 |
| JP | 2006-241015 A | 9/2006 |
| JP | 2007-14871 A | 1/2007 |
| JP | 2007-177131 A | 7/2007 |

OTHER PUBLICATIONS

International Search Report, dated Mar. 9, 2010 in PCT/JP2009/071825.
International Preliminary Report on Patentability and Written Oppinion of the International Searching Authority dated Aug. 9, 2011 for Application No. PCT/JP2009/071825.
Communication Pursuant to Article 94(3) EPC for corresponding European Patent Application No. 09835084.6, dated Jan. 15, 2013.
dos Reis et al., "Transesterification of Brazilian Vegetable Oils with Methanol Over Ion-Exchange Resins," JAOCS, vol. 82, No. 9, pp. 661-665, Sep. 2005.
Extended European Search Report for European Application No. 09835084.6, dated Mar. 27, 2012.
Chinese Office Action, issued Apr. 27, 2013, for corresponding Chinese patent application 200980152607.9 (with English translation).

* cited by examiner

*Primary Examiner* — Sudhakar Katakam
(74) *Attorney, Agent, or Firm* — Birch, Stewart, Kolasch & Birch, LLP

(57) ABSTRACT

The present invention provides a method for producing glycerol, including transesterifying an oil-and-fat with an alcohol in the presence of a solid catalyst to obtain a glycerol product liquid and subjecting the glycerol product liquid to adsorption treatment with an ion-exchange resin.

5 Claims, No Drawings

METHOD FOR PRODUCING GLYCEROL

FIELD OF THE INVENTION

The present invention relates to a method for producing glycerol.

BACKGROUND OF THE INVENTION

Glycerol is generally required to have low level of color (APHA) for practical quality. In purification of glycerol from a crude glycerol, efficient reduction of color (APHA) is thus required. Particularly in production of glycerol that meets Japanese Standards of Cosmetic Ingredients, is employed a method including subjecting the crude glycerol to pretreatments such as distillation and filtration to remove oils and inorganic matters as much as possible, and removing a trace amount of impurities from the treated crude glycerol product liquid or reducing a level of color (APHA) of the treated crude glycerol product liquid (JP-A10-218810 and JP-A6-184024).

JP-A10-218810 discloses production of glycerol using a solid catalyst. EP-A1978009 and US-A2009-030243 disclose purification of glycerol with an ion-exchange resin.

SUMMARY OF THE INVENTION

The present invention provides a method for producing glycerol, including transesterifying an oil-and-fat with an alcohol in the presence of a solid catalyst to obtain a glycerol product liquid and subjecting the glycerol product liquid to adsorption treatment with an ion-exchange resin.

DETAILED DESCRIPTION OF THE INVENTION

Methods of JP-A10-218810 and JP-A06-184024 can produce glycerol in relatively high quality but in decreased yield due to distillation and/or filtration. Distillation and filtration also increase energy costs to make these methods non-economic.

The present invention provides a method that enables to produce high quality glycerol having low level of color (APHA) without requiring pretreatments such as distillation and filtration which lead a decreased yield and increased energy costs. As used herein, the "high quality glycerol" refers that having a level of color (APHA) of 250 or less, preferably 100 or less, more preferably 50 or less, and even more preferably 25 or less as measured by a method described in JIS K-3351 "Glycerol for Industrial Use" (enactment: 26.7.30, revision: 7.1.1).

According to the method for producing glycerol of the present invention, high quality glycerol having a low level of color (APHA) can be produced without requiring pretreatments such as distillation and filtration which lead a decreased yield and increased energy costs.

The method of the present invention is characterized by transesterification of an oil-and-fat with an alcohol in the presence of a solid catalyst to obtain a glycerol product liquid and adsorption treatment of the glycerol product liquid with an ion-exchange resin.

The present invention is a method including transesterifying an oil-and-fat with an alcohol in the presence of a solid catalyst to obtain a crude glycerol and purifying the crude glycerol by adsorption treatment with an ion-exchange resin.

In general, glycerol produced using a homogeneous catalyst requires complicated steps including distillation and filtration before a treatment with an ion-exchange resin. In contrast, the method of the present invention does not require step of distillation, but provides advantages such as an increased yield, decreased production costs and a simplified production.

The glycerol product liquid of the method of the present invention is a glycerol product liquid produced by transesterification of an oil-and-fat with an alcohol in the presence of a solid catalyst.

Examples of the oil-and-fat for the transesterification include vegetable oils such as coconut oil, palm oil, palm kernel oil, soy oil, rapeseed oil, sunflower seed oil, cottonseed oil, peanut oil, and seaweed oil, and animal fats such as beef tallow, lard, and fish oil. These may be used in a purified form.

For the transesterification, a lower alcohol having 1 to 5 carbon atoms is preferably used for the alcohol. Examples of the lower alcohol include methanol, ethanol, propanol and butanol. From the industrial viewpoint, methanol is preferred in terms of low cost and ease of recovering.

The "solid catalyst" used in the transesterification refers that having an alcoholysis activity and being insoluble in a reaction liquid. The present invention can use any solid catalyst without any specific limitation. A solid acid catalyst is preferable, being at least one selected from niobic acid, silica-alumina, silica-titania, silica-zirconia, titania-zirconia, aluminum phosphate, aluminum orthophosphate catalysts, iron phosphates, aluminum sulfate, sulfate ion-supporting zirconia, sulfate ion-supporting titania, antimony pentafluoride-supporting silica-alumina, acid white clay, kaolin, montmorillonite, fluorosulfone resins, synthetic zeolites, and cation-exchange resins. Among these catalyst, aluminum orthophosphate catalysts are preferred, because these have few strong acidic sites and exhibit high selectivity for glycerol. Examples of the aluminum orthophosphate catalyst include alkylphosphonic acid/aluminum phosphate composite catalyst produced by introducing an alkyl group to an aluminum phosphate catalyst.

The reaction may be performed in a batch mode or in a continuous mode, and may in a tank reactor including a stirring device or in a fixed-bed reactor filled with a catalyst. The fixed-bed reactor is preferred, because it does not require separation of the catalyst.

When the reaction is performed in a tank reactor, for achieving sufficient activity and reacting for a short time, an amount of the catalyst used is preferably 1% or more by weight, more preferably 3% or more by weight, and even more preferably 5% or more by weight to the oil-and-fat. For maintaining a sufficiently suspended state by stirring, the amount is preferably 20% or less by weight, more preferably 17% or less by weight, and even more preferably 15% or less by weight to the oil-and-fat. The reaction is usually performed under ambient pressure, or may be performed under pressurized or reduced pressure. Under reduced pressure, the alcohol used can be vaporized at a temperature lower than the boiling point thereof at ambient pressure, and the reaction can progress in a gas (alcohol)-liquid (fat-and-oil)-solid (catalyst) system. At a pressurized pressure, the alcohol is prevented from vaporizing at a temperature higher than the boiling point thereof at the ambient pressure. The reaction will therefore proceed in a liquid (alcohol)-liquid (fat-and-oil)-solid (catalyst) system.

The transesterification can be preferably performed in a fixed-bed reactor filled with the solid catalyst. When the reaction is performed continuously in the fixed-bed reactor, for increasing productivity per unit volume of the reactor and performing the reaction economically, a liquid hourly space velocity (LHSV) based on the fat-and-oil is preferably 0.02/hr or more, more preferably 0.1/hr or more, and even more preferably 0.2/hr or more. For achieving a sufficient reaction yield, the LHSV is preferably 2.0/hr or less, more preferably 1.0/hr or less, and even more preferably 0.7/hr or less.

A reaction system in the fixed-bed reactor may be a two-phase reaction of "liquid (alcohol)-liquid (fat-and-oil)-solid (catalyst)" in which the starting alcohol reacts in the state of liquid, or a three-phase reaction of "gas (alcohol)-liquid (fat-and-oil)-solid (catalyst)" in which the starting alcohol is vaporized. For contact of the alcohol and the fat-and-oil with the solid catalyst, in a liquid-liquid-solid reaction system, a mixed liquid of the alcohol and the fat-and-oil is flowed through the reactor to an upward or downward direction. In a gas-liquid-solid reaction system, the alcohol and the fat-and-oil may contact with the solid catalyst in a gas-liquid parallel-flow or opposite-flow system.

For achieving good reaction rate, a molar ratio of the starting alcohol to the fat-and-oil (based on the assumption that the all fat-and-oil is triglyceride) is 1.5 times or more, more preferably 2 times, and even more preferably 5 times the stoichiometrically required amount. For reducing an amount of a recovered alcohol to conduct the reaction economically, the molar ratio is preferably 50 times or less, more preferably 30 times or less, and even more preferably 15 times or less.

For achieving sufficient catalyst activity to increase a reaction rate and reducing a volume of a reactor required for achieving a desired reaction yield to perform the reaction economically, a reaction temperature is preferably 50° C. or more, more preferably 60° C. or more, even more preferably 80° C. or more, and still even more preferably 130° C. or more. For preventing formation of an ether from bi-produced glycerol analogs such as methoxypropanediol with the starting alcohol, the temperature is preferably 220° C. or less, and more preferably 200° C. or less.

A reaction pressure is preferably 0.1 to 10 MPa, more preferably 0.5 to 8 MPa, and even more preferably 2 to 6 MPa. In a liquid-liquid-solid reaction system, a reaction temperature and a reaction pressure are set according to a vapor pressure of the starting alcohol.

In the present invention, glycerol product liquid prepared by the transesterification in the presence of the solid catalyst as described above are subjected to adsorption treatment with an ion-exchange resin.

Examples of the ion-exchange resin include cation-exchange resins, anion-exchange resins, and mixed resins thereof. Preferred are anion-exchange resins. Specific examples of the cation-exchange resin include DOULITE C-20 (Rohm and Haas Company) and Diaion PK216 (Mitsubishi Chemical Corporation). Specific examples of the anion-exchange resin include DOULITE A113 (Rohm and Haas Company), Diaion WK40 (Mitsubishi Chemical Corporation), and MonoplusMP64 (LEWATIT). Among anion-exchange resins, preferred are porous and high-porous resins. A porous resin refers that having a porous structure produced by physically forming pores (micropores) in a usual gel resin. Specific examples of the porous anion resin include PA306S, PA308 (both, Mitsubishi Chemical Corporation), and Monoplus MP64 (LEWATIT). A resin having high porosity produced by forming many smaller pores than that of a porous resin is referred to as a high-porous resin. Specific examples of the high-porous anion resin include HPA25 (Mitsubishi Chemical Corporation). A surface area of the anion-exchange resin (measured on a dry product by the BET method) is preferably 5 m$^2$/g or more, more preferably 10 m$^2$/g or more, and even more preferably 20 m$^2$/g or more. A pore volume of the anion-exchange resin (measured on a dry product by mercury intrusion porosimetry) is preferably 0.10 ml/g or more, more preferably 0.30 ml/g or more, and even more preferably 0.50 ml/g or more. As used herein, the "dry product" of the anion-exchange resin refers that prepared by drying for 24 hours at 20° C. in vacuo (under 1.33 kPa or less (absolute pressure)) to sufficiently remove moisture.

The adsorption treatment with the ion-exchange resin can be performed by contacting glycerol product liquid with the ion-exchange resin, for example, by flowing glycerol product liquid through a column filled with the ion-exchange resin. In this case, a liquid hourly space velocity (LHSV) is preferably 30/hr or less, more preferably 20/hr or less, and even more preferably 10/hr or less. An amount of glycerol product liquid flowing per ml of ion-exchange resin (liquid passing multiple) is preferably 100 ml-Gly/ml-resin or less, more preferably 50 ml-Gly/ml-resin or less, and even more preferably 20 ml-Gly/ml-resin or less.

In the present invention, for reducing a content of ultraviolet absorbing substances and odor substances, glycerol product liquid may be subjected to adsorption treatment with an adsorbent under alkaline conditions before the adsorption treatment with the ion-exchange resin. For example, a batch process of adding an adsorbent to the glycerol product liquid and mixing or a continuous process of passing the glycerol product liquid through a column filled with an adsorbent can be used.

Examples of the adsorbent include activated charcoal, activated white clay, acid white clay, bentonite, and synthetic zeolite. Among these adsorbents, preferred is activated charcoal, because it has a remarkable large surface area of pore and high adsorbability.

EXAMPLES

The following Examples demonstrate the present invention. Examples are intended to illustrate the present invention and not to limit the present invention.

The present invention will be described in more detail below with reference to Examples and Comparative Examples, but should not be restricted by these Examples.

Catalyst Preparation Example 1

9.9 g of ethylphosphonic acid, 27.7 g of 85% orthophosphoric acid, and 112.5 g of aluminum nitrate (nonahydrate) were dissolved in 1000 g of water. To the solution was added ammonia water dropwise at a room temperature (25° C.) to increase pH to 5. During addition, a white gel was precipitated. The precipitated gel was filtered, washed with water, dried for 5 hours at 110° C., and pulverized to a mesh size of 60 or less. To the pulverized catalyst was added an alumina sol in an amount of 10% of the catalyst. The mixture was extruded into a cylindrical form of 2.5 mm diameter, and calcined for 3 hours at 250° C. to obtain a molded solid acid catalyst (hereinafter, referred to as catalyst 1). The obtained catalyst had a weak acid site of 1 mmol/g, but a strong acid site was out of the detection limit.

Example 1

Transesterification of palm oil and methanol was performed in a fixed-bed reactor filled with the catalyst 1 (reaction temperature: 180° C., reaction pressure: 4.0 MPa, LHSV: 0.42, methanol/palm oil (molar ratio)=10) to obtain a crude glycerol product liquid. Methanol was recovered from the crude glycerol product liquid by a conventional method. Insolubilized oil matters were allowed to separate and removed to obtain a glycerol product liquid. The crude glycerol product liquid was diluted with ion-exchanged water to obtain a glycerol product liquid having a glycerol concentration of 50% by weight. Then 1000 ml of the glycerol product liquid was passed (LHSV=5.3, liquid passing multiple=15.4 ml-Gly/ml-resin), through an anion-exchange resin column [inner diameter: 25 mm, length: 600 mm, an anion-exchange resin (porous resin), Monoplus MP64 (dry surface area: 23.5 m²/g, dry pore volume: 0.53 ml/g), available from LEWATIT, the filled amount: 65 cc] for the ion-exchange resin column. Before passing the glycerol product liquid, the ion-exchange resin column had been treated with a given amount of flowing aqueous solution of 6% sodium hydroxide and washed with water sufficiently for regeneration of the resin.

After the passing, water was removed from the glycerol product liquid by distillation to obtain a purified glycerol. The purified glycerol was measured for color (APHA) in accordance with a method described in JIS K-3351 "Glycerol for industrial use". A result is shown in Table 1.

Example 2

Transesterification of palm oil and methanol was performed in a tank reactor (reaction temperature: 200° C., reaction pressure: 4.0 MPa, reaction time: 5 hours, catalyst amount: 10% by weight, methanol/palm oil (molar ratio)=10) in the presence of a silica-titania powder catalyst (Ti/Si (atom weight ratio)=1/1.7, prepared by an alkoxide method (see, "Preparation of catalyst using a metal alkoxide", page 303, Ueno Akifumi et. al., eds., 1993, IPC.)) to obtain a crude glycerol product liquid. Methanol was recovered from the crude glycerol product liquid by a conventional method. Insolubilized oil matters were allowed to separate and removed to obtain a glycerol product liquid. The crude glycerol product liquid was diluted with ion-exchanged water to obtain a glycerol product liquid having a glycerol concentration of 50% by weight. Then 87 ml of the glycerol product liquid was passed (LHSV=5.3, liquid passing multiple=15.4 ml-Gly/ml-resin), through an anion-exchange resin column [inner diameter: 10 mm, length: 350 mm, anion-exchange resin (porous resin, Monoplus MP64 (dry surface area: 23.5 m²/g, dry pore volume: 0.53 ml/g), available from LEWATIT, the filled amount: 5.6 cc)] for the ion-exchange resin column. Before passing the glycerol product liquid, the ion-exchange resin column had been treated with a given amount of flowing aqueous solution of 6% sodium hydroxide and washed with water sufficiently for regeneration of the resin.

After the passing, water was removed from the glycerol product liquid by distillation to obtain a purified glycerol. The purified glycerol was measured for color (APHA) in the same way as in Example 1. Results are shown in Table 1.

Example 3

A purified glycerol was similarly prepared as in Example 2, except that a catalyst used for transesterification was silica-alumina (silica-alumina catalyst support, grade 135 from Aldrich). The purified glycerol was measured for color (APHA) similarly as in Example 1. A result is shown in Table 1.

Example 4

A purified glycerol was similarly prepared as in Example 1, except that an ion-exchange resin used was an anion resin gel (DOULITE A113 (dry surface area: 0.4 m²/g, dry pore volume: 0.03 ml/g) from Rohm and Haas Company). The purified glycerol was measured for color (APHA) similarly as in Example 1. A result is shown in Table 1.

Comparative Example 1

Transesterification of palm oil and methanol was performed (reaction temperature: 55° C., reaction pressure: ambient, reaction time: 0.5 hours, methanol/palm oil (molar ratio)=1.8, catalyst amount: 0.45% by weight) in the presence of a caustic soda catalyst (homogeneous catalyst system exhibiting alcoholysis activity by dissolving in a reaction liquid) to obtain a crude glycerol product liquid. To the crude glycerol product liquid was added sulfuric acid with stirring to adjust pH to 4.0. Methanol was recovered from the crude glycerol product liquid by a conventional method. Insolubilized oil matters were allowed to separate and removed to obtain a glycerol product liquid. To the glycerol product liquid was added sodium hydroxide to adjust pH to 6.8. The adjusted glycerol product liquid was diluted with ion-exchanged water to obtain a glycerol product liquid having a glycerol concentration of 50% by weight. Then, 1000 ml of the glycerol product liquid was passed (LHSV=5.3, liquid passing multiple=15.4 ml-Gly/ml-resin), through an anion-exchange column [inner diameter: 25 mm, length: 600 mm, anion-exchange resin (porous resin, Monoplus MP64 (dry surface area: 23.5 m²/g, dry pore volume: 0.53 ml/g), available from LEWATIT, the filled amount filled: 65 cc] for the ion-exchange column. Before passing the glycerol product liquid, the ion-exchange resin column had been treated with a given amount of flowing aqueous solution of 6% sodium hydroxide and washed with water sufficiently for regeneration of the resin.

After the passing, water was removed from the glycerol product liquid by distillation to obtain a purified glycerol. The purified glycerol was measured for color (APHA) similarly as in Example 1. A result is shown in Table 1.

Comparative Example 2

A purified glycerol was similarly prepared as in Comparative Example 1, except that an amount of the glycerol product liquid passing through was 333 ml and each of liquid passing multiple and LHSV was one third (i.e., LHSV=1.8, liquid passing multiple-5.1 ml-Gly/ml-resin). The purified glycerol was measured for color (APHA) similarly as in Example 1. A result is shown in Table 1.

TABLE 1

| | Transesterification | | Form of anion-exchange resin | Hue of purified glycerine APHA |
|---|---|---|---|---|
| | Catalyst | Reaction | | |
| Example 1 | catalyst 1*1 | Fixed bed | Porous | 15 |
| Example 2 | silica titania | Stirring tank | Porous | 40 |
| Example 3 | silica alumina | Stirring tank | Porous | 30 |
| Example 4 | catalyst 1 | Fixed bed | Gel | 90 |
| Comparative example 1 | Sodium hydroxide | Stirring tank | Porous | >500 |
| Comparative example 2*2 | Sodium hydroxide | Stirring tank | Porous | >500 |

*1 Ethylphosphoric acid/alminum phosphate composite catalyst prepared in Catalyst preparation example 1.
*2 Embodiment in which the liquid passing multiple and LHSV were one third to Comparative example 1 in the ion exchange treatment.

The invention claimed is:
1. A method for producing glycerol, comprising transesterifying an oil-and-fat with an alcohol in the presence of a solid catalyst to produce a glycerol product liquid and subjecting the glycerol product liquid to adsorption treatment with an ion-exchange resin, wherein the solid catalyst is a solid acid catalyst,
wherein the ion-exchange resin is an anion-exchange resin, and
wherein the glycerol has a level of color (APHA) of 250 or less.

2. The method for producing glycerol according to claim 1, wherein the solid acid catalyst is at least one catalyst selected from the group consisting of niobic acid, silica-alumina, silica-titania, silica-zirconia, titania-zirconia, aluminum phosphate, aluminum orthophosphate catalysts, iron phosphates, aluminum sulfate, sulfate ion-supporting zirconia, sulfate ion-supporting titania, antimony pentafluoride-supporting silica-alumina, acid white clay, kaolin, montmorillonite, fluorosulfone resins, synthetic zeolites and cation-exchange resins.

3. The method for producing glycerol according to claim 2, wherein the solid acid catalyst is an aluminum orthophosphate catalyst.

4. The method for producing glycerol according to claim 1, wherein the anion-exchange resin is a porous or high-porous anion-exchange resin.

5. The method for producing glycerol according to claim 1, wherein the glycerol has a level of color (APHA) of 90 or less.

\* \* \* \* \*